(12) United States Patent
Braumandl

(10) Patent No.: US 7,714,302 B2
(45) Date of Patent: May 11, 2010

(54) APPARATUS FOR DETECTING LASER-STIMULATED LUMINESCENT RADIATION

(75) Inventor: Walter Braumandl, Thurmansbang (DE)

(73) Assignee: Sensor Instruments Entwicklungs- und Vertriebs GmbH, Thurmansbang (DE)

( * ) Notice: Subject to any disclaimer, the term of this patent is extended or adjusted under 35 U.S.C. 154(b) by 355 days.

(21) Appl. No.: 11/826,159

(22) Filed: Jul. 12, 2007

(65) Prior Publication Data

US 2008/0048128 A1 Feb. 28, 2008

(30) Foreign Application Priority Data

Jul. 14, 2006 (DE) .................... 10 2006 032 701

(51) Int. Cl.
*G21H 3/02* (2006.01)
(52) U.S. Cl. .................................... 250/458.1
(58) Field of Classification Search .......... None
See application file for complete search history.

(56) References Cited

U.S. PATENT DOCUMENTS

| | | |
|---|---|---|
| 5,089,709 A | 2/1992 | Chadwick |
| 5,656,783 A | 8/1997 | Frisch et al. |
| 6,252,660 B1 | 6/2001 | Frisch et al. |
| 6,784,441 B2 * | 8/2004 | Ahlers et al. ............. 250/458.1 |
| 6,885,463 B2 | 4/2005 | Ngo |

FOREIGN PATENT DOCUMENTS

| | | |
|---|---|---|
| DE | 1 673 140 | 6/1971 |
| EP | 0 802 499 A2 | 10/1997 |

* cited by examiner

*Primary Examiner*—David P Porta
*Assistant Examiner*—Carolyn Igyarto
(74) *Attorney, Agent, or Firm*—Muncy, Geissler, Olds & Lowe, PLLC

(57) ABSTRACT

An apparatus is disclosed for inspecting a surface containing a material that emits luminescent radiation in response to absorbing excitation radiation. The apparatus comprises a laser disposed in or adjacent to a housing. A sensor opening is defined in the housing and permits emission of excitation radiation generated by the laser and permits admission of the luminescent radiation emanating from the surface in response to the excitation radiation. A sensor monitors whether ambient light is being admitted between an edge of the sensor opening and the surface upon which the sensor opening is in contact. A safety circuit permits the laser to be actuated only when the sensor detects a substantially or completely light-impermeable contact between the edge of the sensor opening and the surface.

17 Claims, 2 Drawing Sheets

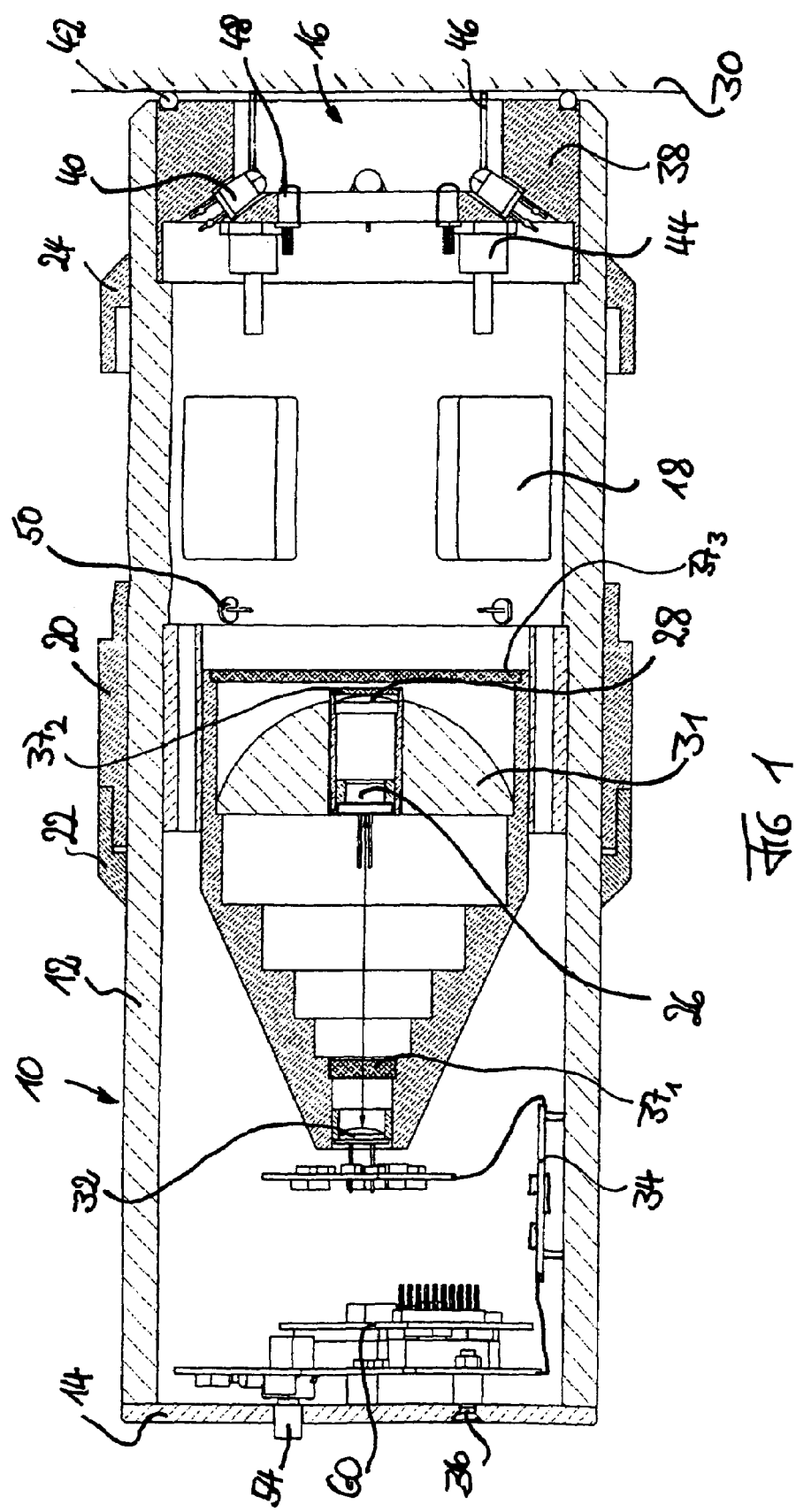

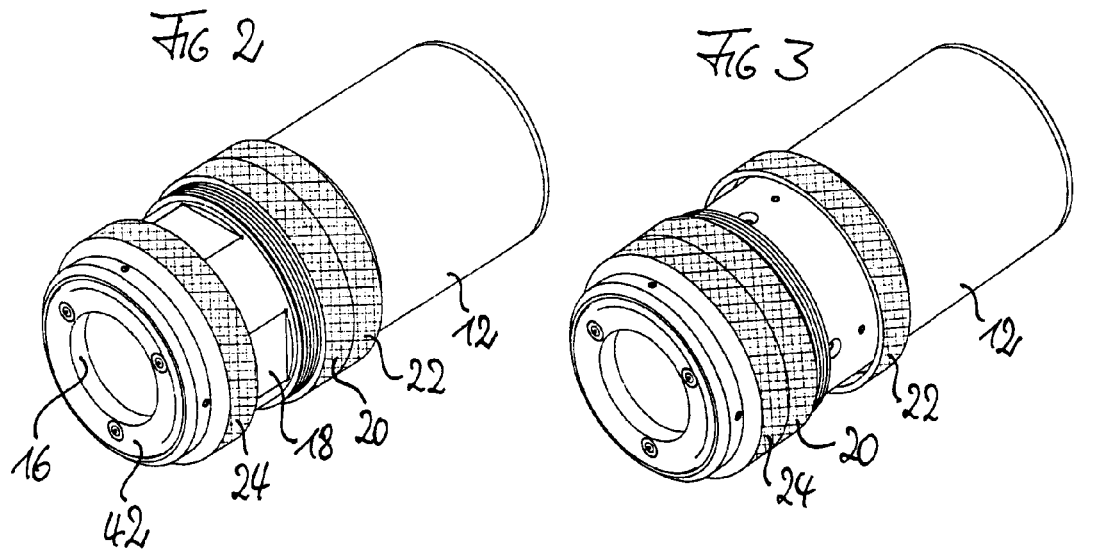
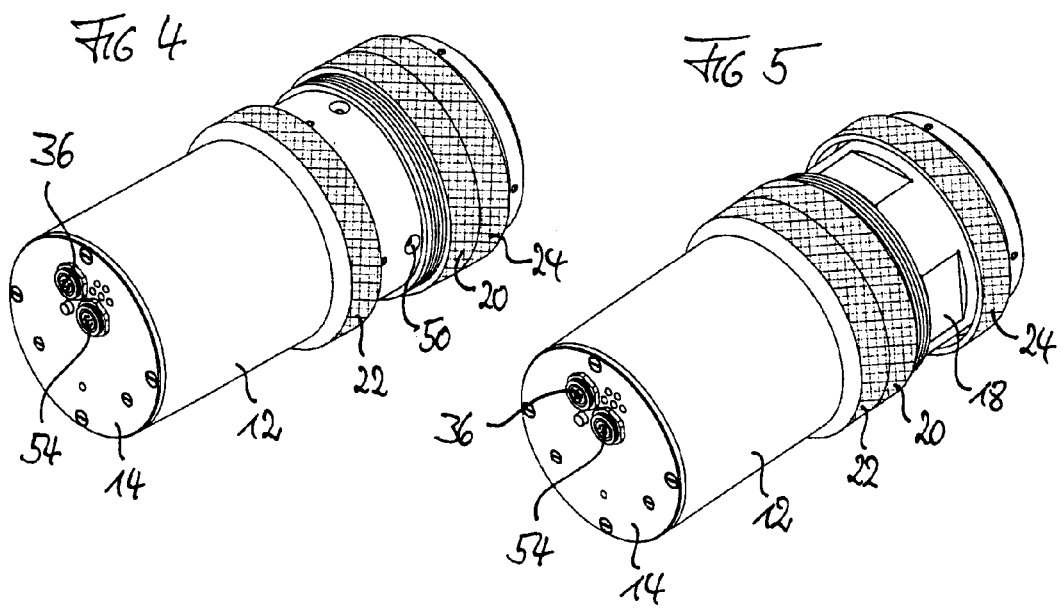
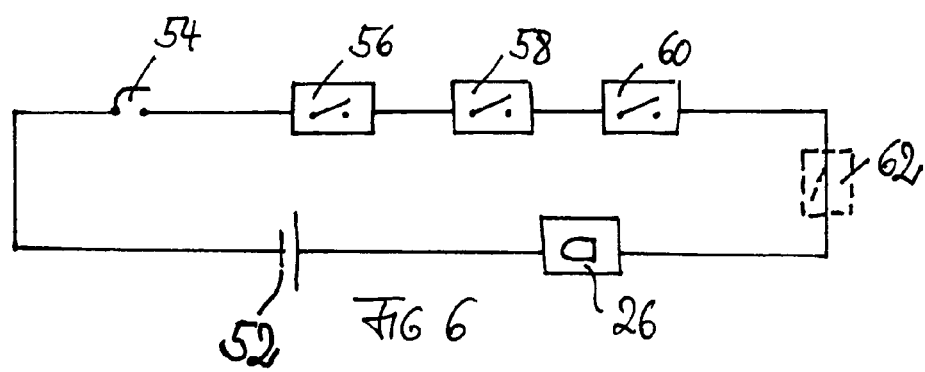

APPARATUS FOR DETECTING LASER-STIMULATED LUMINESCENT RADIATION

CROSS-REFERENCE

This application claims priority to German patent application number 10 2006 032 701.2 filed Jul. 14, 2006, the contents of which are incorporated herein as if fully set forth herein.

TECHNICAL FIELD

The invention concerns an apparatus for detecting laser-stimulated luminescent radiation and more particularly safety features thereof that are capable of preventing potentially dangerous usage of the apparatus.

BACKGROUND ART

In the modern economy, reliable identification of products has been accorded increasing importance not only for improved logistics, but also for preventing product piracy. Recently, "luminescent nano-pigments" (LNPs) have been utilized to provide products with a permanent, distinguishable, spectral fingerprint that is visible only upon appropriate optical stimulation. Such LNPs can be provided as non-toxic, bio-compatible, stable and very long-lasting inorganic materials that are introduced into the product surfaces and are not modifiable therein. The LNPs are stable at high and low temperatures, are insensitive to solar radiation and are available in particle sizes of, e.g., 0.3 μm to 60 μm. When irradiated, e.g., with laser radiation, they can be excited to luminesce. The delay or lag of the luminescent radiation relative to the excitation irradiation can be practically zero (fluorescence) or can have predetermined values that are characteristic for the respective LNPs.

An apparatus for detecting laser-stimulated luminescent radiation is known from European Patent Application No. 0 802 499 A2. This apparatus has an opening designed for the emission of excitation irradiation, generally in the UV-range, generated by a semiconductor diode housed in the housing of the apparatus and for the admission of luminescent radiation, generally in the visible range, that emanates from a surface of an object as a result the excitation radiation applied thereto. However, this apparatus lacks a safety mechanism for preventing, e.g., the user's eyes from being accidentally exposed to harmful excitation irradiation.

An apparatus for examining objects such as currency, paintings, stamps, etc. using UV-light is known from German patent publication no. 1 673 140. This apparatus has a downward-opening housing for irradiating the object and for monitoring the luminescence emanating therefrom. During the inspection process, the UV-lamp and the object are disposed in the apparatus housing so that the UV-light is confined therein. Consequently, the design of this apparatus does not lend itself to convenient, e.g., portable, inspection of a wide-variety of product sizes.

SUMMARY OF THE INVENTION

An object underlying the invention is to provide methods and apparatus for inspecting on-site and in a safe manner a wide variety of object surfaces having or containing materials or particles, such as LNPs, that emit detectable radiation upon being irradiated. Such inspected surfaces can be, e.g., packaging surfaces or the surfaces of the products themselves, including edible products.

According to one aspect of the present teachings, an apparatus for detecting laser-stimulated luminescent radiation is taught. This apparatus preferably has a housing formed with a sensor opening and a laser contained in the housing. The sensor opening is preferably arranged and constructed to permit excitation radiation generated by the laser to exit the housing and to admit luminescent radiation generated or emitted by an object surface in response to the excitation radiation. The apparatus preferably further includes a device for monitoring contact between the edge of the sensor opening and the object surface and a safety circuit that permits the laser to be turned-on or illuminated only when a light-impermeable contact, as detected by the contact-monitoring device, exists between the edge of the sensor opening and the object surface.

The laser for generating the excitation radiation may preferably be an infra red (IR) laser, Class 3B. As a result of the design and safety measures taught herein, the apparatus can be safely operated in such a manner that it fulfills the specifications of a Class 1 laser in spite of the relatively high-power laser contained therein. A Class 1 laser is safe for use under all reasonably-anticipated conditions of use; in other words, it is not expected that the maximum permissible exposure (MPE) can be exceeded. A Class 3B laser produces light of an intensity such that the MPE for eye exposure may be exceeded and direct viewing of the beam is potentially serious.

In further aspects of the present teachings, the device for monitoring the contact between the edge of the sensor opening and the object surface preferably includes at least one photo-sensitive element disposed in the interior of the housing. This photo-sensitive element preferably is arranged and constructed to detect visible and/or ambient light that has present in the interior of the housing, e.g., through the sensor opening.

In addition or in the alternative, an elastically-resilient, projecting bead or ring may preferably partially or completely surround the edge of the sensor opening so as to contact and/or seal with the object surface during inspection, so as to prevent the excitation irradiation from irradiating anything other than the object surface.

In addition or in the alternative, one or more contact switches may be disposed along or near the edge of the sensor opening. The contact switches are preferably arranged to contact the object surface and to generate a corresponding signal upon contact. In this case, the safety circuit preferably permits the laser to be turned-on or illuminated only when a contact, preferably a flush or sealing contact that does not permit light therethrough, is detected as existing between the object surface and at least one of the elastic bead or ring and/or an edge of the sensor opening.

In addition or in the alternative, at least one photo-sensitive sensor may be affixed on or to the housing for the detection of ambient light outside the housing. In this case, the safety circuit is preferably adapted to permit the laser to be turned-on or illuminated only when ambient light is detected as being present outside the apparatus housing.

In addition or in the alternative, a manually-actuatable switch may be provided for turning-on the laser. In this case, the manually-actuatable switch is preferably arranged and constructed to turn-on or illuminate the laser only when the safety circuit is in a state, in which the laser is permitted to be turned-on.

In addition or in the alternative, at least one light source may be disposed in the housing for illuminating the sensor opening and/or the interior of the apparatus. This light source is preferably connected to the contact switch(es) and is arranged and constructed to be turned on or illuminated when the apparatus is not contacting the surface in a flush and/or light impermeable manner.

In addition or in the alternative, the housing may preferably comprise at least one viewing window, through which the sensor opening is visible. The at least one viewing window is preferably provided on a side of the apparatus or in any position that permits the user to look through the viewing window in order to determine whether the sensor opening is properly aligned with a suitable portion of the object surface to be inspected. More preferably, such a viewing window is substantially or completely impermeable to the wavelength(s) of the laser excitation radiation.

In addition or in the alternative, a movable cover is preferably provided for covering the viewing window when the object surface is to be inspected by the apparatus. Such cover is preferably slidably disposed on the housing. In addition or in the alternative, the cover is preferably adapted to cover the ambient light sensor when the viewing window is uncovered.

In addition or in the alternative, the apparatus is preferably constructed as a self-contained handheld unit, e.g., a portable and/or battery-operated unit.

In addition or in the alternative, the apparatus may include a terminal adapted for connecting data processing circuitry contained in the apparatus with an external data processor.

These and other objects, features and advantages of the present teachings will become apparent upon reading the following detailed description of the preferred embodiments, with references to the appended drawings and the claims.

BRIEF DESCRIPTION OF THE DRAWINGS

FIG. 1 shows a longitudinal cross-section through an apparatus according to the present teachings, FIGS. 2 to 5 show various perspective views of the apparatus with a sliding ring shown in an opened or closed position relative to the viewing window, and FIG. 6 shows a block diagram of a preferred user protection or safety circuit.

DETAILED DESCRIPTION OF THE PREFERRED EMBODIMENTS

As shown in FIG. 1, an inventive apparatus preferably comprises a housing 10 that is comprised or made, e.g., of metal and/or synthetic material. The housing 10 preferably includes a cylindrical body 12 that is closed by a closing wall 14 on the left-side of FIG. 1, although the cross-sectional shape of the housing is not limited. The housing 10 opens on the right side to form a sensor opening or cavity 16, which is preferably circular in cross-section, since a circular cross-sectional opening permits a flush contact with both flat and spherical surfaces. However, the shape or cross-section of the sensor opening or cavity 16 can be modified in accordance with the intended application of the apparatus and thus, the shape of the opening is not limited.

A plurality of viewing windows 18 are preferably equally spaced around the circumferential direction of the housing 10, although a single viewing window 18 may be sufficient in certain applications, for enabling the user to visually align the sensor opening 16 with a portion of the object surface to be inspected. The viewing window(s) 18 preferably comprise(s) a glass and/or synthetic material that is substantially or completely impermeable for the wavelength(s) of radiation generated by a laser 26 disposed in the housing, e.g. infra red radiation.

The viewing windows 18 can be open and closed (or covered and uncovered) with a sliding ring 20 that is displaceable on the housing 10 between an uncovered position (see e.g. FIGS. 1, 3 and 4) and a covered position (see e.g., FIGS. 2 and 5). Appendages of the sliding ring 20 can be provided with threads that correspond with threads provided on a left-side stop ring 22 and a right-side stop ring 24, respectively. The stop rings 22, 24 preferably define the slidable limits of the sliding ring 20. Moreover, that the left-side and right-side threads preferably may be used to respectively secure the open and closed positions of the sliding ring 20. However, the sliding ring 20 can also be secured or affixed in the respective limit positions using other affixing or retaining means, such as bayonets, clips, snap-lock arrangements, latches, etc.

The laser 26 disposed in the housing 10 generates excitation irradiation at a wavelength or in a range of wavelengths that is/are absorbable by the luminescent material associated with the article or object to be inspected. In a particularly preferred embodiment, the laser 26 is, e.g., an infra red laser diode of Class 3B having a pulsed power output of 1 Watt, a pulse length of 300 microseconds and a pulse interval of 3 milliseconds, although the laser specifications necessarily must be chosen based upon the intended application of the apparatus, e.g., based upon the type of luminescent material that will be detected.

The radiation emitted by the laser 26 is preferably focused or dispersed by a lens 28 such that excitation radiation is directed to exit through the sensor window 16. Luminescent radiation, which is emitted by a surface 30 of an examined object containing the luminescent material located directly outside the sensor window 16 upon excitation by the laser irradiation, enters into the apparatus through the sensor window or cavity 16. The luminescent radiation is preferably focused by a lens 31 onto a receiver 32, e.g., a sensor, adapted to detect the luminescent radiation. The specifications of the receiver 32 naturally must be selected based upon the wavelength(s) of luminescent radiation emitted by the object surface (30) to be inspected. The laser 26 and the lens 28 are preferably located in the center of the lens 31, although other arrangements are certainly possible.

The receiver 32 is preferably connected with an evaluation unit 34 contained within the apparatus. The evaluation unit 34, e.g., a microprocessor or other analysis circuitry, is preferably adapted to evaluate or analyze the received luminescent radiation according to frequency, intensity and/or the temporal delay or lag of the emission of the luminescent radiation with respect to absorption of the excitation radiation emitted by the laser 26. The analyzed information can then be compared with target or reference values stored in a memory of the evaluation circuit. In addition or in the alternative, a terminal 36 may be provided for inputting target or reference values and/or for reading-out measured results from the evaluation unit 34. In this case, the evaluation circuit 34 can be connected to an external computer or other processor via the terminal 36. However, in some embodiments, it is not necessary to provide the evaluation unit 34 in the housing 10; rather the terminal 36 may electronically couple measured data from the receiver 32 to an external processor for purposes of evaluation. An indicating and/or display unit, e.g., an acoustic or optical display unit, can be provided on the closing wall 14 or elsewhere on the housing for indicating and/or displaying the measured and/or analyzed result(s).

In particularly preferred embodiments, glass coverings and/or plates $37_1, 37_2, 37_3$, having appropriate light/radiation transmission (pass) band ranges are located directly on the right side of the receiver 32, the lens 28 and the lens 31 as shown in FIG. 1. For example, the glass plate $37_1$ is advantageously an IR-blocking filter.

Since the measuring process, i.e. the generation of the luminescent radiation and the evaluation thereof, is not a particularly preferred aspect of the present invention, it will not further be described in detail herein. Any radiation measuring and evaluation technique known in the art may be advantageously utilized with the present teachings to provide a suitable inspection apparatus.

The elements, which are provided for safely operating the apparatus, will now be explained in greater detail.

At least one, and more preferably four, visible-light emitting LEDs 40, which are preferably white-light LEDs, is/are preferably attached in an equally distributed manner around the circumferential direction on an annular insertion part 38 that is inserted into and/or disposed within the right-side of the cylindrical body 12. The center of the annular insertion part 38 may advantageously form the sensor window/cavity 16 that is illuminable with the visible light from LEDs 40. In particular, it is preferred that the visible light from the LEDs 40 illuminates both the interior of the sensor opening/cavity 16 (i.e. within the housing 10), as well as the surrounding outer area adjacent to the sensor window 16 and the housing 10.

Furthermore, a circumferential or annular-shaped, elastic component, e.g., an elastically-deformable O-ring 42, is preferably disposed on the outer front side of the annular insertion part 38. Naturally, it is only necessary that this elastically-resilient component be positioned on or near the outer edge of the sensor opening 16 so as to contact the surface 30 of the object or material to be inspected. Also, the shape of the elastic member can be modified as appropriate based upon the particular cross-sectional shape of the sensor opening 16 and the particular application of the inspection apparatus (e.g., the shape of the object surfaces 30 to be inspected). Finally, in certain applications of the present teachings, an electrically-resilient component is not necessary if the edge(s) of the sensor opening 16 is (are) capable of a light-impermeable, or substantially light-impermeable contact or seal with the surface 30 to be inspected.

At least one, more preferably four, micro-switches 44 is/are preferably also provided around the circumferential direction of the housing 10 in an equally distributed manner. The push buttons 46 of the micro-switches 44 preferably project into a plane defined by the front side of the not-deformed O-ring 42 so at to contact the surface 30 of the object or material to be inspected. However, the switch(es) 44 may be configured in another ways as long as the switch(es) 44 are capable of detecting whether the sensor opening 16 is in contact with the surface 30. Thus, resistances and/or capacitance switches may be appropriate in certain applications and/or light-based switches also may be appropriate. The nature and construction of the switch(es) 44 is not particularly limited.

At least one, more preferably four, photo-sensitive sensors 48 is/are equally spaced around the circumferential direction and is/are preferably provided on a radially-inwardly projecting annular flange of the annular insertion part 38 for detecting visible and/or ambient light present within the sensor window/cavity 16, i.e. within the interior of the right-side of the housing 10. The location and construction of the sensor(s) 48 may be changed as appropriate as long as it is possible to detect whether visible and/or ambient light (preferably above or below a predetermined threshold) is present in the sensor opening/cavity 16.

In addition, at least one, more preferably four, photo-sensitive sensors 50 is/are equally distributed around the circumferential direction of the housing 10 and is/are preferably disposed on or in the surface of the housing 10. The sensor(s) 50 is/are preferably adapted to detect ambient light present outside of the housing 10. Further, the sensor(s) 50 is/are preferably not covered by the sliding ring 20 when the sliding ring 20 is located in the position closing the viewing window 18 (see FIG. 4).

FIG. 2 shows a perspective view of the apparatus from the side of the sensor window 16 with an uncovered viewing window 18. FIG. 3 shows the view of FIG. 2 when the sliding ring 20 is disposed in the closed position.

FIG. 4 shows a perspective view of the apparatus from the side of the closing wall 14, wherein the sliding ring 20 is disposed in its closing position and the sensors 50 are uncovered for detecting ambient light present outside of the housing.

FIG. 5 shows the view of FIG. 4 when the sliding ring 20 is disposed in the open position and the viewing window 18 are uncovered.

FIG. 6 shows a schematic circuit that is preferably provided in the apparatus, in which reference number 52 denotes a current source and reference number 54 denotes a manually actuatable switch.

Reference number 56 denotes a first switch that is actuated by the photo-sensitive sensors 48 that detect visible light present in the interior of the sensor opening/cavity 16 and/or the housing 10. The switch 56 is preferably arranged and constructed to be opened when at least one of the sensors 48 detects visible light.

Second switch 58 is actuated by one or more of the micro-switches 44 and is only closed when all micro-switches 44 are closed, i.e. the push-buttons 46 of the micro-switches 44 are pushed back by a certain threshold amount due to the apparatus being pressed against the surface 30 to be examined. Thus, the second switch 58 preferably functions to confirm a tight seal, e.g., a light-impermeable seal, of the sensor opening 16 against the surface 30 to be inspected.

Third switch 60 is actuated by the photo-sensitive sensors 50 that detect ambient light outside the housing 10 and is opened as soon as none of the sensors 50 detect ambient light. That is, the third switch 60 is closed when at least one of the sensors 50 detects ambient light, thereby indicating the inspection of the object surface 30 is not taking place in the dark.

As can be readily derived from FIG. 6, when the manual control switch 54 is actuated (closed), the laser 26 is then activated or energized only when all of the first, second and third switches 56, 58, 60 are closed. The switches 56, 58, 60 thus form a part of a safety circuit that is disposed in the interior of the housing 10 and, if necessary, has its own microprocessor. The manual actuation switch 54 preferably protrudes, e.g., from the closing wall 14 so that it is conveniently actuatable by the user. However, the manual actuation switch 54 can take any form, such as e.g. a touch switch, that enables the user to control when the laser 26 is actuated.

The apparatus, which is advantageously constructed as a self-contained handheld unit, preferably functions as follows:

The sliding ring 20 is first brought into the closed position shown in FIGS. 1, 2 and 5. In this position, the ambient light sensors 50 are covered so that the third switch 60 assigned to the ambient light sensors 50 opens. Another, not-illustrated switch preferably closes in response to the opening of the third switch 60 so as to connect the LEDs 40 with the current source 52.

As a result, the LEDs 40 illuminate so that the apparatus, which is set upon or otherwise contacts the surface 30 for inspection purposes, can be aligned with a marking or other indication provided on the to-be-examined surface 30. This alignment can be performed by observing through the viewing window 18, which is preferably formed as an IR-blocking filter, to determine that the sensor opening 16 is located at an appropriate location on the surface 30.

When the apparatus has been properly aligned with respect to the surface 30, the sliding ring 20 is then moved from the position shown in FIG. 2 into the position shown in FIG. 3, so that the sliding ring 20 covers the viewing window 18 and uncovers the ambient light detecting sensors 50, which preferably causes the LEDs 40 to go out or extinguish.

Then, the apparatus is pressed firmly against the surface 30 in the aligned position, thereby slightly inwardly deforming the O-ring 42 and causing the buttons 46 of the micro-switches 44 to be moved inwardly into the housing 10, thereby closing the micro-switches 44. The O-ring 42 acts as a light-impermeable enclosure or barrier with the surface 30, thereby blocking visible (ambient) light from entering into the interior of the apparatus, i.e. into the inner portion of the sensor opening/cavity 16. When no ambient light is present inside the housing 10 (e.g., within the sensor opening 16), the sensors 48, which are preferably sensitive only to visible light, sense no light and thus indicate darkness inside the sensor opening 16, thereby closing the first switch 56. If the sensors 50 detect visible (ambient) light present outside of the housing 10, the third switch 60 connected to the sensors 50 also is closed.

As was explained above, when all switches 56, 58 and 60 are closed, the IR-laser 26 can be actuated or energized when the manually actuatable switch 54 is actuated or closed, e.g., by pressing the switch 54 with the same hand that is holding the apparatus or more preferably with the other hand that is not holding and pressing the apparatus against the surface 30. Since the sensors 48 are preferably not sensitive to the wavelength(s) of the radiation (e.g., infra red) emitted by the laser 26, the second switch 56 remains closed when the laser 26 is illuminated. In order to prevent the second switch 56 connected the sensors 48 from opening when the surface 30 thereafter begins to emit luminescent radiation, if necessary, the sensors 48 also can be switched to an inoperative state during the period of time, in which the luminescence, which lags the excitation radiation, is emitted.

As long as the manual actuation switch 54 remains actuated in this state, a measurement cycle or operation thus takes place, in which the laser 26 emits excitation radiation and the surface 30 emits luminescent light that is received by the receiver 32 and is preferably evaluated by the evaluation unit 34. The evaluation or analysis of the received radiation can, as was described above, preferably take place directly within the apparatus and can be indicated on an indicator unit that is provided on the apparatus, e.g., by LEDs. In addition or in the alternative, the measured data can be transmitted to an external computer for evaluation or detailed indication/display.

It is noted that a condition or state can exist, in which all micro-switches 44 are closed, but the apparatus is nevertheless so uneven with the to-be-examined surface 30 that the abutment of the housing 10 on the surface 30 is not impermeable to light. In other words, excitation radiation emitted by the laser 26 could escape from the sensor opening 16 in direction that might be harmful to the user or someone or something else in the vicinity.

In this case, if the measurement were permitted to take place in ambient darkness and the IR radiation can be emitted in a direction other than solely against the surface 30, a danger also could arise to the user, etc., (if the third switch 60 connected to the sensors 50 is not provided) because infra red laser radiation is not visible, whereby eye or other sensitive tissues, materials, etc. could be injured or damaged. In order to prevent the occurrence of such a danger, the third switch 60 is closed only when ambient light is present outside the housing (as detected by the sensors 50), so that it is ensured that the sensors 48 actually detect a light-impermeable abutment or contact of the apparatus (i.e. the sensor opening 16) on the surface 30.

The safety of the apparatus can be further increased by providing an additional switch 62 (drawn with a dotted line in FIG. 6) that only closes when the sliding ring 20 is detected as being in the position, in which the sensors 50 are uncovered and the viewing windows 18 are covered or blocked.

To that end, the apparatus can be further modified so that the LEDs 40 are connected with the current source 52 contained in the housing 10, e.g., a battery that is rechargeable via a terminal in the closing wand 14, via a switch contained in the stop ring 22 that is adapted to close when the sliding ring 20 abuts the stop ring 22. The annular insertion part 38 can be provided with an inner threading or a bayonet or another attachment device, in which a cover is insertable when it is not being used. A window having low reflectivity and high permeability can be provided at the position of the cover. The first switch 54 can be omitted in some embodiments, wherein the laser 26 is automatically turned-on as soon as all switches 56, 58, 60 are closed.

The exemplary-described apparatus, with which the safety requirements of a Class 1 laser are fulfilled in spite of the higher-power excitation laser of Class 3B being utilized, can be modified in various ways. The numbers of the utilized sensors, switches, etc. can be changed. The type of sensors, switches, etc. can likewise be changed. It is simply preferred the safety functions are realized, with which it is ensured that the laser is activated only when it is determined or confirmed that the apparatus is in a light-impermeable abutment/contact on the to-be-examined surface, so that no dangerous laser light, or at most an amount of laser light that equal to or less than a Class 1 laser, can penetrate to the outside.

REFERENCE NUMBER LIST

10 Housing
12 Body
14 Closing wall
16 Sensor window
18 Viewing window
20 Sliding ring
22 Stop ring
24 Stop ring
26 Laser
28 Lens
30 Surface
31 Lens
32 Receiver
34 Evaluation unit
36 Terminal
37 Glass plate
38 Annular insertion part
40 LED
42 O-ring
44 Micro-switch
46 Push button
48 Sensor
50 Sensor
52 Current source 54 Manually actuatable switch
56 First switch
58 Second switch
60 Third switch
62 Switch

The invention claimed is:

1. An apparatus for inspecting a surface containing a material that emits luminescent radiation in response to absorbing excitation radiation, comprising:
a housing,
a laser disposed in or adjacent the housing,
a sensor opening defined in the housing and being arranged and constructed to permit emission of excitation radiation generated by the laser and to permit admission of the luminescent radiation emanating from the surface in response to the excitation radiation,
a sensor arranged and constructed to monitor whether ambient light is being admitted between an edge of the sensor opening and the to-be-inspected surface when the surface is in contact with the sensor opening,
a safety circuit arranged and constructed to permit the laser to be actuated only when the sensor detects an at least substantially completely light-impermeable contact between the edge of the sensor opening and the surface; and
at least one ambient light sensor disposed on or in the housing, wherein the safety circuit is further arranged and constructed to permit the laser to be actuated only when the ambient light sensor detects ambient light around the housing.

2. An apparatus according to claim 1, wherein the sensor includes at least one photo-sensitive element disposed within the interior of the housing and arranged and constructed to detect ambient light penetrating into the housing through the sensor opening.

3. An apparatus according to claim 2, further comprising an elastically-resilient material substantially or completely surrounding the edge of the sensor opening and being positioned for contact with the surface to be inspected.

4. An apparatus according to claim 3, further comprising at least one contact switch disposed along or near the edge of the sensor opening in a position for contacting the surface to be inspected, wherein the safety circuit is further arranged and constructed to permit the laser to be actuated only when the at least one contact switch detects that a contact exists between the elastically-resilient material and the surface to be inspected.

5. An apparatus according to claim 1, further comprising a manually-actuatable switch electrically coupled to the laser, wherein manually-actuatable switch is arranged and constructed to effect actuation of the laser only when the safety circuit is in a state permitting the laser to be actuated.

6. An apparatus according claim 5, further comprising at least one light source disposed in the housing for illuminating the sensor opening from the inside of the housing.

7. An apparatus according to claim 6, wherein the housing comprises at least one viewing window, through which the sensor opening is visible.

8. An apparatus according to claim 7, wherein the viewing window is at least substantially impermeable to the excitation radiation.

9. An apparatus according to claim 8, further comprising a movable cover disposed on the housing and being arranged and constructed to cover and uncover the viewing window.

10. An apparatus according to claim 9, wherein the cover is arranged and constructed to cover the ambient light sensor disposed in or on the housing when the viewing window is uncovered and wherein the light source is adapted to illuminate when the ambient light sensor is covered.

11. An apparatus according claim 10, wherein the apparatus is constructed as a self-contained handheld unit.

12. An apparatus according to claim 11, further comprising:
a processor disposed in the housing and being adapted to process data representing the luminescent radiation emanating from the surface under inspection, and
a terminal adapted to connect the processor with an external data processor.

13. An inspection apparatus for inspecting a surface containing a material that emits luminescent radiation in response to absorbing excitation radiation, comprising:
a first means for sensing whether a sensor opening of the inspection apparatus is in contact with the surface to be inspected,
a second means for sensing any ambient light present inside a sensor cavity, the sensor cavity being defined in the inspection apparatus and being in communication with the sensor opening and a laser contained in the inspection apparatus,
a third means for permitting the laser to be energized to emit radiation only when the sensor opening is detected as being in contact with the surface to be inspected and any ambient light present in the sensor cavity is detected in an amount equal to or less than a first predetermined threshold and
a fourth means for illuminating a source of visible light disposed inside the inspection apparatus when the first means does not detect the sensor opening as being in contact with the surface to be inspected.

14. An inspection apparatus according to claim 13, further comprising a fifth means for detecting whether ambient light is present outside the inspection apparatus and
wherein the third means is arranged and constructed to energize the laser to emit radiation only when:
(i) the first means detects the sensor opening as being in contact with the surface to be detected,
(ii) the second means detects ambient light present in the sensor cavity in an amount equal to or less than the first predetermined threshold and
(iii) the fifth means detects ambient light present outside the inspection apparatus in an amount equal to or above a second predetermined threshold.

15. An inspection apparatus according to claim 13, further comprising a manually-actuatable switch electrically connected with the third means, the laser and a current source, the manually-actuatable switch being arranged and constructed to cause the laser to be energized by the current source only when the first means detects the sensor opening as being in contact with the surface to be inspected and the second means detects any ambient light present in the sensor cavity is in an amount that is equal to or less than the first predetermined threshold.

16. A method for inspecting a surface containing a material that emits luminescent radiation in response to absorbing excitation radiation, comprising:
sensing whether a sensor opening of an inspection apparatus is in contact with the surface to be inspected,
sensing any ambient light present inside a sensor cavity, the sensor cavity being defined in the inspection apparatus and being in communication with the sensor opening and a laser contained in the inspection apparatus,
permitting the laser to be energized to emit radiation only when the sensor opening is detected as being in contact with the surface to be inspected and any ambient light present in the sensor cavity is detected in an amount equal to or less than a first predetermined threshold, and illuminating a source of visible light disposed inside the inspection apparatus when the sensor opening is not detected as being in contact with the surface to be inspected.

17. A method according to claim 16, further comprising detecting any ambient light present outside the inspection apparatus and wherein the laser is energized to emit radiation only when the sensor opening is detected as being in contact with the surface to be detected, ambient light present in the sensor cavity is detected in an amount equal to or less than the first predetermined threshold and ambient light present outside the inspection apparatus is detected in an amount equal to or above a second predetermined threshold.

* * * * *